(12) United States Patent
Angold et al.

(10) Patent No.: US 10,238,522 B2
(45) Date of Patent: Mar. 26, 2019

(54) EXOSKELETON DEVICE AND METHOD OF IMPEDING RELATIVE MOVEMENT IN THE EXOSKELETON DEVICE

(71) Applicant: Ekso Bionics, Inc., Richmond, CA (US)

(72) Inventors: Russ Angold, American Canyon, CA (US); Kurt Amundson, Berkeley, CA (US)

(73) Assignee: Ekso Bionics, Inc., Richmond, CA (US)

( * ) Notice: Subject to any disclaimer, the term of this patent is extended or adjusted under 35 U.S.C. 154(b) by 0 days.

(21) Appl. No.: 15/508,588

(22) PCT Filed: Sep. 3, 2015

(86) PCT No.: PCT/US2015/048377
§ 371 (c)(1),
(2) Date: Mar. 3, 2017

(87) PCT Pub. No.: WO2016/036963
PCT Pub. Date: Mar. 10, 2016

(65) Prior Publication Data
US 2017/0281385 A1    Oct. 5, 2017

Related U.S. Application Data

(60) Provisional application No. 62/046,545, filed on Sep. 5, 2014.

(51) Int. Cl.
*A61F 5/01* (2006.01)

(52) U.S. Cl.
CPC .......... *A61F 5/0102* (2013.01); *A61F 5/0123* (2013.01); *A61F 2005/0158* (2013.01); *A61F 2005/0167* (2013.01)

(58) Field of Classification Search
CPC ........ A61F 5/01; A61F 5/0106; A61F 5/0102; A61F 5/0123; A61F 2005/0158;
(Continued)

(56) References Cited

U.S. PATENT DOCUMENTS

| | | |
|---|---|---|
| 2,558,986 A | 7/1951 | Seelert |
| 2,573,866 A | 11/1951 | Murphy |

(Continued)

FOREIGN PATENT DOCUMENTS

| | | |
|---|---|---|
| EP | 302148 | 2/1989 |
| JP | 2012239709 | 12/2012 |
| WO | 2014/093470 | 6/2014 |

*Primary Examiner* — Tarla R Patel
(74) *Attorney, Agent, or Firm* — Diederiks & Whitelaw, PLC

(57) ABSTRACT

An exoskeleton device includes a first brace coupled to a first portion of a wearer of the exoskeleton device and a second brace coupled to a second portion of the wearer. A first joint connects the first and second braces and allows relative movement between the first and second braces. A first brake is controllable between an unactuated state and a plurality of actuated states, and the first brake impedes relative movement between the first and second braces at the first joint while the first brake is in one of the plurality of actuated states. A manual actuator is selectively used by the wearer during relative movement between the first and second braces. Use of the actuator causes the first brake to enter one of the plurality of actuated states such that relative movement between the first and second braces is impeded at the first joint.

19 Claims, 4 Drawing Sheets

(58) Field of Classification Search
CPC ...... A61F 2005/0167; A61F 2005/0155; A61F 2005/0165
See application file for complete search history.

(56) References Cited

U.S. PATENT DOCUMENTS

| | | | |
|---|---|---|---|
| 4,108,451 A | 8/1978 | Scheck, Sr. | |
| 4,456,003 A | 6/1984 | Allard et al. | |
| 4,602,627 A | 7/1986 | Vito et al. | |
| 4,697,808 A | 10/1987 | Larson et al. | |
| 4,711,242 A | 12/1987 | Petrofsky | |
| 4,760,850 A | 8/1988 | Phillips et al. | |
| 4,982,732 A | 1/1991 | Morris | |
| 5,176,042 A | 1/1993 | Bean et al. | |
| 5,378,224 A | 1/1995 | Billotti | |
| 5,476,441 A | 12/1995 | Durfee et al. | |
| 5,490,831 A | 2/1996 | Myers et al. | |
| 5,891,061 A | 4/1999 | Kaiser | |
| 6,080,123 A | 6/2000 | Pansiera | |
| 6,969,365 B2 | 11/2005 | Scorvo | |
| 6,979,304 B2 | 12/2005 | Nijenbanning et al. | |
| 7,410,472 B2 | 8/2008 | Yakimovich et al. | |
| 7,947,004 B2 | 5/2011 | Kazerooni et al. | |
| 7,985,193 B2 | 7/2011 | Thorsteinsson et al. | |
| 7,988,652 B2 | 8/2011 | Chao | |
| 8,079,967 B2 | 12/2011 | Ikeuchi et al. | |
| 8,087,498 B2 | 1/2012 | Dupuis et al. | |
| 9,662,261 B2 | 5/2017 | Julin et al. | |
| 2007/0123997 A1 | 5/2007 | Herr et al. | |
| 2012/0259259 A1* | 10/2012 | Chugunov | A61F 5/0102 602/16 |
| 2013/0102935 A1 | 4/2013 | Kazerooni et al. | |
| 2015/0051528 A1* | 2/2015 | Gilbert | A61F 5/01 602/16 |

\* cited by examiner

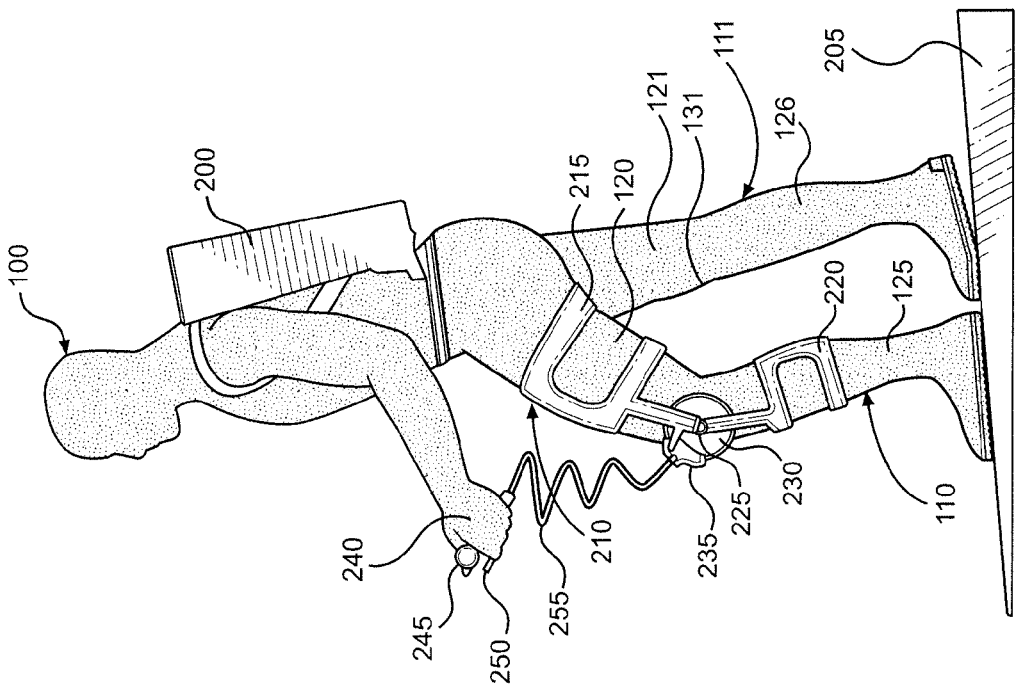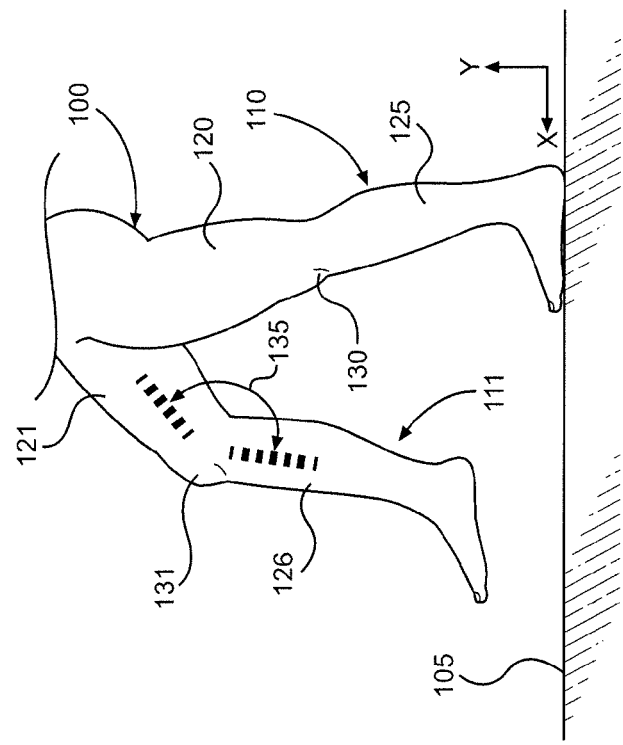

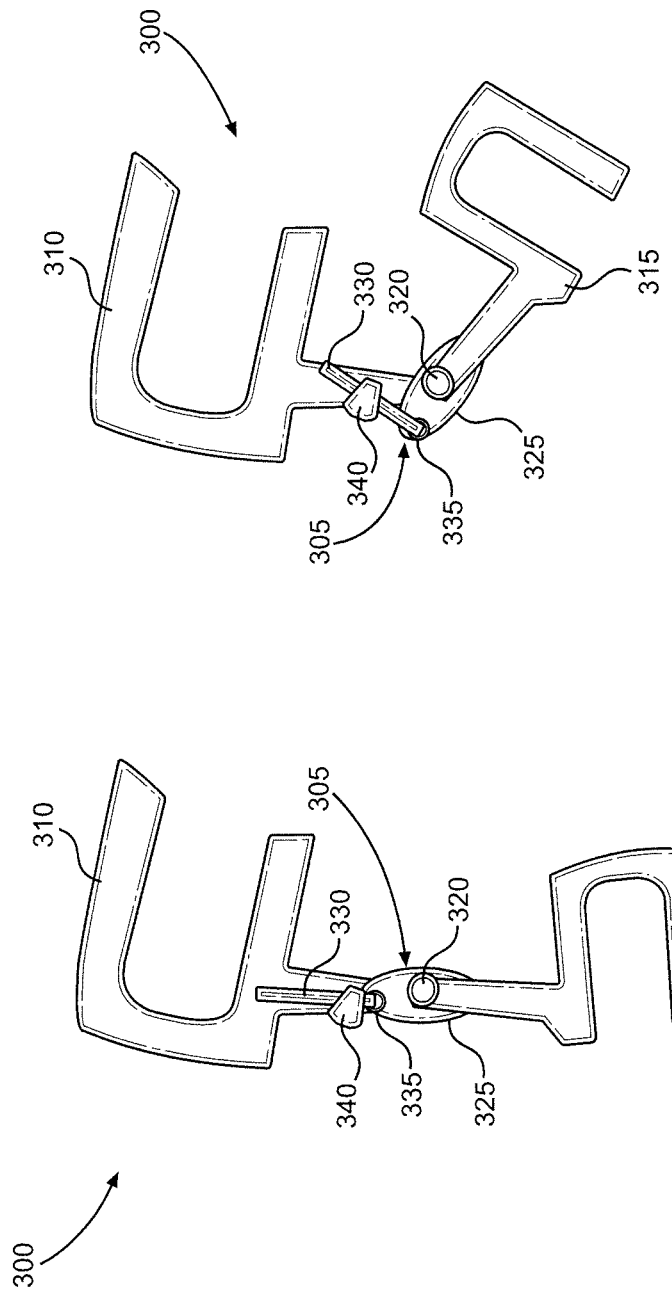

EXOSKELETON DEVICE AND METHOD OF IMPEDING RELATIVE MOVEMENT IN THE EXOSKELETON DEVICE

CROSS-REFERENCE TO RELATED APPLICATIONS

This application represents a National Stage application of PCT/US2015/048377 filed Sep. 3, 2015 and titled "Exoskeleton Device and Method of Impeding Relative Movement in the Exoskeleton Device" which claims the benefit of U.S. Provisional Patent Application Ser. No. 62/046,545, which was filed on Sep. 5, 2014 and titled "Unpowered Exoskeletal Orthoses for Load Sharing Applications". The entire content of this application is incorporated herein by reference.

FIELD OF THE INVENTION

The present invention relates to a devices and methods that augment a user's carrying capacity and/or aid in the prevention of injury during the performance of certain motions or tasks. More particularly, the present invention relates to devices and methods suitable for use by a person engaging in walking or descending while bearing weight. These devices include a set of artificial limbs that potentiate improved function of the person's appendages for activities including, but not limited to, walking while bearing weight with greater endurance and/or decreased risk of injury or allowing for more weight to be supported while walking.

BACKGROUND OF THE INVENTION

Human exoskeleton devices are often used for load carriage, rehabilitation and strength augmentation. However, these devices generally have large power supplies, complex actuators and high costs that make them impractical for applications for which they would otherwise be well suited. For example, recreational hikers and backpackers are often limited not by aerobic endurance, but rather by joint pain and musculoskeletal injuries. These injuries are caused by the carrying of relatively low loads (on the order of 50 lb) straining muscles and damaging joints. Indeed, after their youthful years, hikers are often known to complain that the factor limiting their cherished recreation is not any aerobic limit, but rather the inability of their knees to handle the battering they endure coming down hills. As the issue for these hikers is the dissipation of energy, a powered system is not required. Rather, it would be desirable to design an unpowered system that does not require any electronics or batteries, dramatically decreasing the cost and/or weight of the system compared to other exoskeletons. Furthermore, the hiker would not need to be concerned with the device running out of power and becoming useless, nor being spoiled by weather conditions.

SUMMARY OF THE INVENTION

It is an object of the present invention to provide a device and method that allows for a person to limit or obstruct the rate of movement about the knee and or hip joint of the leg(s) of that person and, specifically, to allow the person to limit or obstruct the rate of flexion about the knee and/or hip joint of the leg(s) while descending over a sloped surface. Also, it is an object of the present invention to allow for the operation of this device without electrical power or electronic systems.

It is an additional object of the present invention to provide a device and method that allows for a person to use a knee and/or hip movement limiting device to also absorb the weight of a load carried by the person, such as a backpack being worn by the person, allowing for the transfer of the weight of the backpack around the person and to the surface.

Concepts were developed wherein a rotary braking system is integrated into an orthotic exoskeleton device, which may be fitted to the leg of a person for example. The wearer of this exoskeleton device uses a hydraulically actuated handbrake to resist motion about a joint. In one simple embodiment, the brake system can include a small disc brake, possibly a bicycle disk brake. Such a brake includes a lever with an associated plunger that displaces hydraulic fluid when the person squeezes the lever with his hand. The plunger is connected to a small hydraulic hose that in turn connects to a brake caliper fitted over a brake rotor. When fluid is displaced by squeezing the handle, the caliper on the other end of the hydraulic hose clamps onto the brake rotor. These brakes are well understood and widely used in bicycles. Some such brakes may instead use a cable or wire rope (often in the form of a Bowden cable) to transfer force from the handle to the caliper, and these are generally suitable as well. In this simple embodiment, the brake rotor is connected to exoskeleton structure on one side of a joint, and the caliper is connected to the structure on the other side of the joint. In the first embodiment of the present invention, this brake device is described on the knee joint, but it should be understood that this technique could be applied equally about other joints, such as the hip, the elbow or the shoulder, to name a few. The person wearing the exoskeleton can selectively actuate the brake to slow or stop motion of the knee joint. This is highly advantageous when the person is descending a slope or stair because the high knee joint moments that result during such an activity can be borne by the exoskeleton, thereby avoiding injury to the person. Because bicycle brakes, especially on mountain bicycles, are intended to brake slightly more than the mass of a person (i.e., the weight of the person and the bicycle) at speeds slightly higher than someone might wish to walk or run, bicycle brakes as designed will provide more than sufficient braking power.

Concepts were developed wherein the brake rotor is unrolled to be a linear, or other non-rotary configuration, and arranged in such a way that, as the knee joint rotates, the moment arm between the point of action of the brake caliper and the center of rotation of the knee joint varies, resulting in different effective amounts of braking action at different angles. Rotary brakes make sense in wheeled applications, but human legs do not have continuous motion. A rotary brake will always apply the same braking force for the same force input on the handle at all angles of the brake, which may be disadvantageous in the case of a human exoskeleton. Biomechanically, when a person's knee is nearly straight (i.e., completely extended), the loads from his body generate nearly zero torque about the knee. As a result, a person trying to control the motion with the brake would find that even the slightest force on the handle would result in the knee being completely locked. Only when a person's knee was very flexed and his/her body generated substantial knee torque would pressing the lever give them the ability to control their knee motion (of course, the brake could be scaled to provide very little resistance, but this only reverses the problem, providing good resolution at low torques but no ability to resist high torques). To overcome this disadvantage, the brake rotor is unrolled to be linear in accordance with the invention and arranged in such a way that, as the knee joint rotates, the moment arm between the point of action of the brake caliper and the center of rotation of the knee joint varies, resulting in different effective amounts of braking action at different angles. By appropriate design of the mechanism, the brake cancels the nonlinearities of the person's leg and results in a more intuitive joint braking operation.

Concepts were further developed wherein the knee brake-equipped exoskeleton device is attached to the waist belt of a backpack with a simple rotary or flexural joint and to a boot worn by the wearer, thereby allowing the exoskeleton device to bear some of the weight of the backpack. In some embodiments, the exoskeleton can simply be a knee brace. In this case, the torque generated at the knee joint is reacted at the thigh and shank of the person. Although such embodiments are considered to be rather simple and light, they have two disadvantages: they do not directly unload the weight of anything the person may be carrying (either on his back, in his arms or even with an upper body exoskeleton), and reacting large torques on the thigh or shank of the person will cause discomfort. In a preferred embodiment, the exoskeleton extends at least from the hip to the ankle. As a result, the torque generated at the knee by the brake can be reacted over a large distance, resulting in a lower exoskeleton-person interaction force and generally making the device more comfortable. Furthermore, if the exoskeleton reaches the ground below the ankle, possibly with a foot or boot, and extends to the upper body, it can bear the vertical weight of the load as well (i.e., transfer the load directly to the supporting surface). In some embodiments, the person might be carrying a load in a backpack with its own structure and waist belt. In such an embodiment, the exoskeleton can attach to the waist belt of the backpack with a rotary or flexural joint, thereby allowing flexion, extension, rotation and/or abduction/adduction of the hip. This embodiment is advantageous because the resulting exoskeleton can be very light since it uses the already available structure of the backpack. Also, the exoskeleton can be designed to adjustably connect to a range of commercially available backpacks at the belt or external frame of the backpack.

Concepts were further developed wherein a braking system was fitted to multiple joints on an orthotic exoskeleton device, preferably fitted to the leg of a person. The wearer of this exoskeleton device is able to actuate the handbrake, causing the rotary braking system to limit the rotation of both the knee and the hip of the leg about which this exoskeleton device is fitted. In some embodiments, it can be desirable to link the motion of several joints together. For example, during stair and steep slope descent, it can be desirable to brake the motion of both the knee and the hip together. In doing so, it is generally desirable to keep to one brake handle per hand so that the person does not need to change which brake is in use during walking. Using one brake actuator for control of multiple joints can be achieved in several ways. First, when the brake system is hydraulic, the hydraulic lines for two calipers, at the right hip and right knee for example, can be plumbed to the same handle. Then, when force is applied to the handle, both joints will be simultaneously braked. The same can be done on the left side, with the person using a second brake handle in his left hand to control those joints. In some embodiments, the person might not control the ratio of forces between the joints in real time, but it is possible, through judicious choices of brake and joint geometry, to keep the ratios in line with those seen in normal biomechanical data.

In particular, the present invention is directed to an exoskeleton device and a method of impeding relative movement in the exoskeleton device. The exoskeleton device comprises a first brace configured to be coupled to a first portion of a wearer of the exoskeleton device and a second brace configured to be coupled to a second portion of the wearer. A first joint connects the first and second braces and is configured to allow relative movement between the first and second braces. A first brake is controllable between an unactuated state and a plurality of actuated states, the first brake being configured to impede relative movement between the first and second braces at the first joint while the first brake is in one of the plurality of actuated states. A manual actuator is configured to be selectively used by the wearer during relative movement between the first and second braces, wherein use of the actuator causes the first brake to enter one of the plurality of actuated states such that relative movement between the first and second braces is impeded at the first joint. Preferably, the exoskeleton device does not include a power source or a control system.

In one embodiment, the actuator is a handbrake. The handbrake is connected to the first brake by a first brake line, and use of the handbrake actuates the first brake by transmission of force through the first brake line. The first brace is configured to be coupled to an upper leg of the wearer. When the second brace is configured to be coupled to a lower leg of the wearer, the first joint is a knee joint. When the second brace is configured to be coupled to a torso of the wearer, the first joint is a hip joint, and the second brace can be a backpack or a belt of a backpack.

In another embodiment, a third brace is configured to be coupled to a third portion of the wearer. A second joint connects one of the first and second braces to the third brace and is configured to allow relative movement between the one of the first and second braces and the third brace. A second brake is controllable between an unactuated state and a plurality of actuated states, the second brake being configured to impede relative movement at the second joint while the second brake is in one of the plurality of actuated states. Use of the handbrake causes the second brake to enter one of the plurality of actuated states such that relative movement is impeded at the second joint. The handbrake is connected to the second brake by a second brake line, and use of the handbrake actuates the second brake by transmission of force through the second brake line. The first and second brake lines can be connected such that use of the handbrake actuates one of the first and second brakes by transmission of force through both the first and second brake lines. In one embodiment, the first brace is configured to be coupled to an upper leg of the wearer, the second brace is configured to be coupled to a lower leg of the wearer and the third brace is configured to be coupled to a torso of the wearer, with the first joint being a knee joint and the second joint being a hip joint.

In a further embodiment, the first brake includes a rotor and a caliper, and use of the actuator causes the caliper to engage the rotor. Alternatively, the first brake includes a linear brake shoe and a caliper, and use of the actuator causes the caliper to engage the linear brake shoe. In one embodiment, the manual actuator is selectively used while the wearer of the exoskeleton device descends over a sloped surface.

Additional objects, features and advantages of the invention will become more readily apparent from the following detailed description of the invention when taken in conjunction with the drawings wherein like reference numerals refer to corresponding parts in the several views.

BRIEF DESCRIPTION OF THE FIGURES

FIG. 1 is a side view of the lower appendages of a person with one knee in a flexed position;

FIG. 2 is a side view of a person walking downhill while coupled to an exoskeleton device equipped with a rotary knee braking device;

FIG. 3A is a side view of an exoskeleton device equipped with a non-rotary brake caliper-shoe, with the exoskeleton device shown in the knee extended (i.e., leg straight) position;

FIG. 3B is a side view of the exoskeleton device of FIG. 3A in the knee flexed position;

DETAILED DESCRIPTION OF THE PREFERRED EMBODIMENTS

Figure 4:
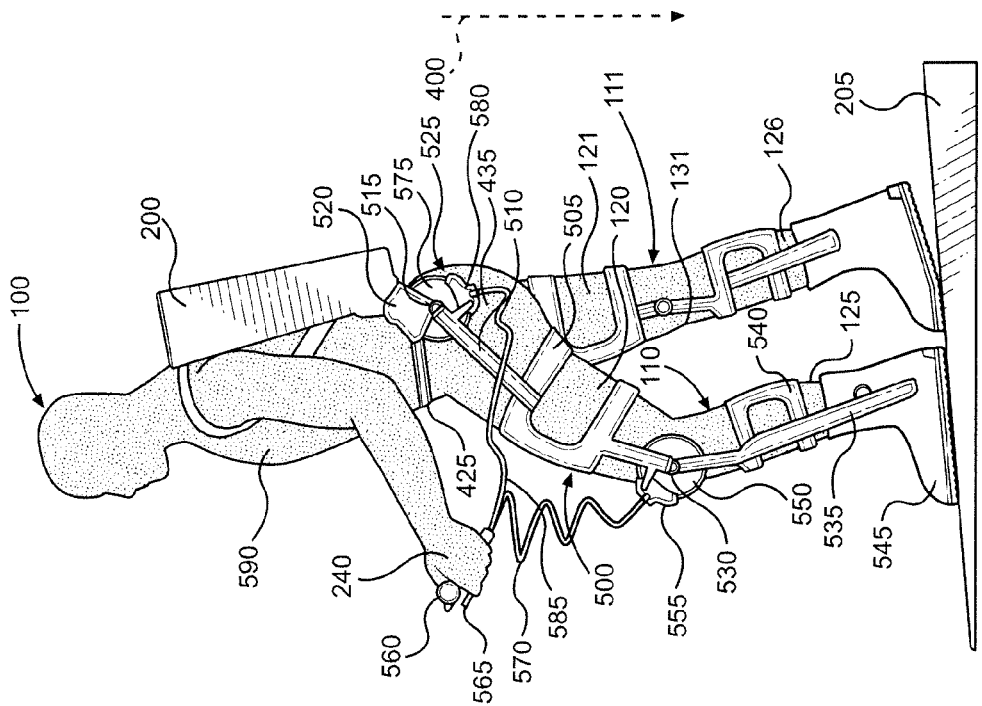
FIG. 4 is a side view of a person walking downhill while coupled to an exoskeleton device equipped with a knee braking device, with the exoskeleton device coupled to the backpack, legs and boots of the person.

Detailed embodiments of the present invention are disclosed herein. However, it is to be understood that the disclosed embodiments are merely exemplary of the invention that may be embodied in various and alternative forms. The figures are not necessarily to scale, and some features may be exaggerated or minimized to show details of particular components. Therefore, specific structural and functional details disclosed herein are not to be interpreted as limiting, but merely as a representative basis for teaching one skilled in the art to employ the present invention.

With initial reference to FIG. 1, the lower body of a person 100 is shown standing upon a surface 105. Specifically, person 100 has legs 110 and 111, with upper and lower portions of leg 110 labeled 120 and 125 and upper and lower portions of leg 111 labeled 121 and 126. Legs 110 and 111 also have knees labeled 130 and 131, respectively. Leg 111 is shown flexed at knee 131 to a flexion angle 135.

With reference now to FIG. 2, a first embodiment of the present invention is illustrated. Person 100, wearing a backpack 200, is walking downhill on a surface 205. An exoskeleton device 210 is fitted to leg 110 of person 100. A thigh brace 215 of exoskeleton device 210 is coupled to upper leg 120 of person 100, and shank brace 220 of exoskeleton device 210 is coupled to lower leg 125 of person 100. Exoskeleton device 210 rotates at an exoskeleton knee joint 225, which is collocated with knee 130 of leg 110. A rotor 230 is attached to shank brace 220 and rotates about exoskeleton knee joint 225. The rotation of rotor 230 and exoskeleton knee joint 225 is limited by the action of a caliper 235. Caliper 235 is attached to thigh brace 215, with caliper 235 in close proximity to and selectively interacting with rotor 230. Person 100 controls the action of caliper 235 by using a hand 240 to squeeze a handbrake body 245 and a handbrake lever 250 to transmit a force through a brake line 255 to caliper 235. This force causes caliper 235 to engage, or contact, rotor 230. As caliper 235 engages rotor 230, the rotational movement of rotor 230 about exoskeleton knee joint 225 is impeded. Since rotor 230 is connected to shank brace 220, which is coupled to lower leg 125, and caliper 235 is attached to thigh brace 215, which is coupled to upper leg 120, the action of caliper 235 has the effect of limiting the movement of thigh brace 215 and upper leg 120 relative to shank brace 220 and lower leg 125 and reducing the rate of flexion at knee 130. Although FIG. 2 illustrates the use of the present invention in connection with leg 110 of person 100, it should be understood that an exoskeleton device can be coupled to each of legs 110 and 111. Similarly, although FIG. 2 illustrates the use of the present invention in connection with a knee joint, it should be understood that, in other embodiments, this technique can be applied equally about other joints, such as the hip, the elbow or the shoulder.

In the simplest embodiment, the brake system includes a small disc brake, possibly a bicycle disk brake. In such an embodiment, the brake rotor is connected to exoskeleton structure on one side of a joint, and the brake caliper is connected to the structure on the other side of the joint, as discussed above in connection with FIG. 2. In some embodiments, the force transmitted by the handbrake body and brake line is effected by a change in the displacement of hydraulic fluid, where the brake system includes a lever with associated plunger that displaces hydraulic fluid when the person squeezes the lever with their hand. The plunger is connected to a small hydraulic hose (i.e., the brake line) that in turn connects to the caliper, which is fitted over the rotor. When fluid is displaced by squeezing the lever, the caliper on the other end of the hydraulic hose clamps onto the rotor. In other embodiments, such brakes can instead use a cable or wire rope (often in the form of a Bowden cable) to transfer force from the handle to the caliper, and these are generally suitable as well. Both types of brakes are well understood and widely used in bicycles.

As an example of the first embodiment, consider a person who is backpacking over a long distance that includes a downhill descent. During the descent, the person uses the knee braking system of the first embodiment to resist the motion at his knees, thereby limiting the stress upon his knees. This both decreases the risk of injury and possibly allows the person to either increase his rate of travel or weight carried relative to that person without the device of the first embodiment.

Turning to FIGS. 3A and 3B, a second embodiment of the present invention is illustrated. FIG. 3A shows an exoskeleton device 300, equipped with a linear braking device 305, in a fully extended knee position, and FIG. 3B shows exoskeleton device 300 in a flexed knee position. As with exoskeleton device 210, exoskeleton device 300 is comprised of a thigh brace 310 that is rotatably connected to a shank brace 315 at an exoskeleton knee joint 320. Shank brace 315 is connected to a shank extension 325, and a linear brake shoe 330 is connected to shank extension 325 by a pivot joint 335. Linear brake shoe 330 passes through and in close proximity with a caliper 340. Caliper 340 is connected to thigh brace 310 and selectively interacts with linear brake shoe 330. Specifically, the person wearing exoskeleton device 300 controls the action of caliper 340 by using a handbrake or other device, as discussed above in connection with FIG. 2. As caliper 340 engages, or contacts, linear brake shoe 330, the rotational movement of shank extension 325 about exoskeleton knee joint 320 is impeded. Since shank extension 325 is connected to shank brace 315 and caliper 340 is connected to thigh brace 310, the action of caliper 340 has the effect of limiting the movement of thigh brace 310 relative to shank brace 315 about exoskeleton knee joint 320. As knee joint 320 of exoskeleton device 300 rotates, the moment arm between the point of action of brake caliper 340 and the center of rotation varies, resulting in different effective amounts of braking action at different knee angles. By appropriate design of the mechanism, linear braking device 305 can cancel the biomechanical nonlinearities of the wearer's leg and provide a more intuitive operation, as compared to the operation of a rotary brake device. Although FIGS. 3A and 3B illustrate the use of the present invention in connection with a knee joint, it should be understood that, in other embodiments, this technique can be applied equally about other joints, such as the hip, the elbow or the shoulder.

As an example of the second embodiment, consider a person who is downhill skiing over uneven snow. During descent, the person uses the knee braking system of the second embodiment to resist the motion at his knees, thereby limiting the stress upon his knees. However, due to uneven terrain and variable rates of speed, the forces exerted upon the knees of this person are highly variable, requiring rapid adjustments by the person and complicating the control of the braking system. The device of the second embodiment is designed so as to take into account the biomechanical nonlinearities of the person's leg and provide a more intuitive user operation, as compared to operation of a rotary brake device. In particular, the moments resolved by the human knee are generally larger when the knee angle is large because, when the knee angle is large, the trunk weight is displaced farther from the knee pivot, increasing the resulting moment. The nonlinear moment arm of the second embodiment roughly but effectively mirrors the changing moment arm of the load, resulting in simpler and more intuitive operation of the device. Improved ease of operation of the device increases the amount of force at the knees that is absorbed by the exoskeleton device, which reduces stress to the person's knees, decreasing the risk of injury and possibly allows the person to increase speed or performance in certain maneuvers.

With reference to FIG. 4, a third embodiment of the present invention is illustrated. Person 100, who is wearing backpack 200, is walking downhill on surface 205. The downward force exerted by the weight of backpack 200 is represented by a dotted arrow 400. An exoskeleton device 405 is fitted to legs 110 and 111 of person 100, although, for simplicity, only the portion of exoskeleton device 405 fitted to leg 110 is described below. A thigh brace 410 of exoskeleton device 405 is coupled to upper leg 120 of person 100, and a thigh link 415 is connected to thigh brace 410. Thigh link 415 is rotatably connected to a hip pivot joint 420, with hip pivot joint 420 being coupled to a belt 425 of backpack 200 at a thigh-backpack connection 430 on a hip 435 of person 100. A shank brace 440 of exoskeleton device 405 is coupled to the lower leg 125 of person 100, and shank brace 440 is connected to a shank link 445. Shank link 445 is rotatably connected to thigh link 415 at a knee joint 450, and shank link 445 is rotatably connected to a boot 455, with boot 455 being worn by leg 110 of person 100. Exoskeleton device 405 rotates at exoskeleton knee joint 450, which is collocated with the knee 130 of leg 110 of person 100. A rotor 460 is attached to shank link 445 and rotates about exoskeleton knee joint 450. The rotation of rotor 460 and exoskeleton knee joint 450 is limited by the action of a caliper 465. Caliper 465 is attached to thigh link 415, with caliper 465 in close proximity to and selectively interacting with rotor 460, which is attached to shank link 445. Person 100 controls the action of caliper 465 by using hand 240 to squeeze a handbrake body 470 and a handbrake lever 475 to transmit a force through a brake line 480 to caliper 465. This force cause caliper 465 to engage, or contact, rotor 460. As caliper 465 engages rotor 460, the rotational movement of rotor 460 about exoskeleton knee joint 450 is impeded. Since rotor 460 is connected to shank link 445, which is connected to shank brace 440, with shank brace 440 being coupled to lower leg 125, and caliper 465 is attached to thigh link 415, which is connected to thigh brace 410, with thigh brace 410 being coupled to upper leg 120, the action of caliper 465 has the effect of limiting the movement of thigh link 415 and upper leg 120 relative to shank link 445 and lower leg 125 and reducing the rate of flexion at knee 130. Some or all of the force 400 exerted by the weight of backpack 200 is transferred around person 100 through exoskeleton device 405 in this embodiment. Specifically, force 400 is transmitted from backpack 200 to belt 425 at thigh-backpack connection 430, and force 400 is then transmitted through hip pivot joint 420 to thigh link 415. Thigh link 415 transfers force 400 over knee joint 450 to shank link 445, and shank link 445 transmits force 400 to boot 455, which ultimately transfers force 400 to surface 205. Although the embodiment of FIG. 4 utilizes a rotary braking device, the linear braking system of the second embodiment is also suitable for use in such an embodiment and may, in some cases, be preferred.

As an example of the third embodiment, consider a person who is on a multi-day backpacking trip over a long distance that includes a downhill descent. Due to the length of the backpacking trip, the person needs to carry more supplies, which translates into more backpack weight than this person finds comfortable (or safe) to bear during descent in the absence of the device of this embodiment. During descents, the person uses the knee braking and backpack support system of the third embodiment to resist the motion at his knees, thereby limiting the stress that would otherwise be exerted upon his knees both by his own weight and the weight of the backpack. Thus, the device of this embodiment both decreases the risk of injury and possibly allows the person to travel farther with the weight of his backpack, as compared with that person without the device.

Figure 5A:
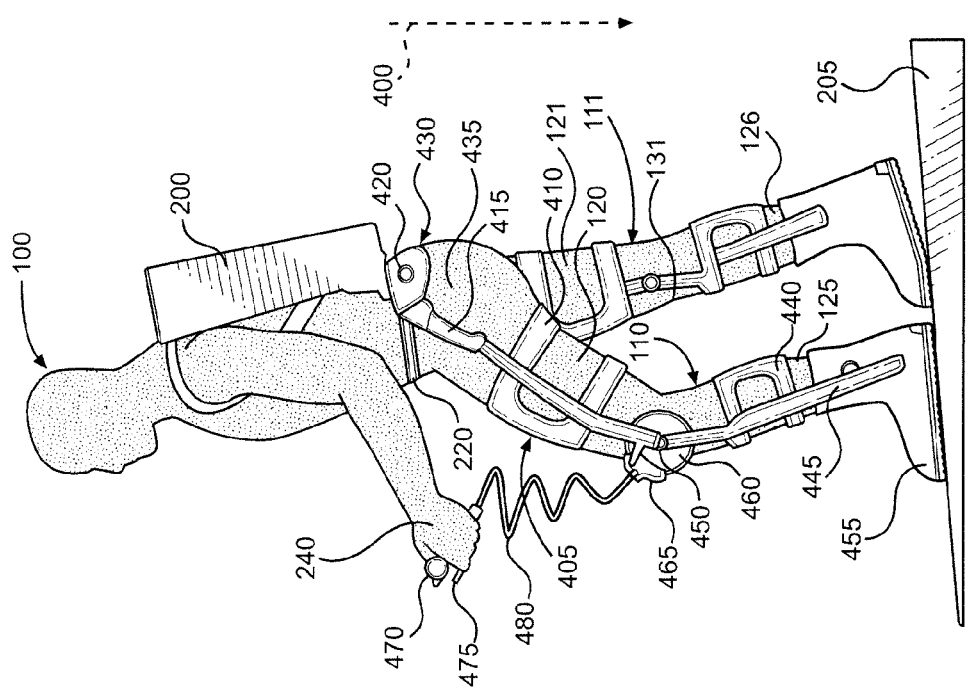
FIG. 5A is a side view of a person walking downhill while coupled to an exoskeleton device equipped with both a knee braking device and a hip braking device, with the exoskeleton device coupled to the backpack, legs, and boots of the person.

With reference now to FIG. 5A, a fourth embodiment of the present invention is illustrated. Person 100, who is wearing backpack 200, is walking downhill on surface 205. The downward force exerted by the weight of backpack 200 is represented by dotted arrow 400. An exoskeleton device 500 is fitted to legs 110 and 111 of person 100 although, for simplicity, only the portion of exoskeleton device 500 fitted to leg 110 is described below. A thigh brace 505 of exoskeleton device 500 is coupled to upper leg 120 of person 100, and thigh link 510 is connected to thigh brace 505. Thigh link 510 is rotatably connected to an exoskeleton hip joint 515, with exoskeleton hip joint 515 rotatably connected to a hip-backpack connection 520. Hip-backpack connection 520 is coupled to belt 425 of backpack 200 at a thigh-backpack connection 525 on hip 435 of person 100. Thigh brace 505 of exoskeleton device 500 is rotatably coupled to an exoskeleton knee joint 530, and exoskeleton knee joint 530 is also rotatably coupled with a shank link 535. Shank link 535 is connected to a shank brace 540, which is coupled to lower leg 125 of person 100. Shank link 535 is also rotatably connected to a boot 545, with boot 545 being worn by leg 110 of person 100. A knee rotor 550 is attached to shank link 535 and rotates about exoskeleton knee joint 530. The rotation of knee rotor 550 and exoskeleton knee joint 530 is limited by the action of a knee caliper 555. Knee caliper 555 is attached to thigh brace 505, with knee caliper 555 in close proximity to and selectively interacting with knee rotor 550, which is attached to shank link 535. Person 100 controls the action of knee caliper 555 by using hand 240 to squeeze a handbrake body 560 and a handbrake lever 565 to transmit a force through a first brake line 570 to knee caliper 555. This force causes knee caliper 555 to engage, or contact, knee rotor 550. As knee caliper 555 engages rotor knee 550, the rotational movement of knee rotor 550 about exoskeleton knee joint 530 is impeded. Since knee rotor 550 is connected to shank link 535, which is connected to shank brace 540, with shank brace 540 coupled to lower leg 125, and knee caliper 555 is attached to thigh brace 505, which is coupled to upper leg 120, the action of knee caliper 555 has the effect of limiting the movement of thigh brace 505 and upper leg 120 relative to shank link 535, shank brace 540 and lower leg 125 and reducing the rate of flexion at knee 130.

Similarly, a hip rotor 575 is attached to hip-backpack connection 520 and rotates about exoskeleton hip joint 515. The rotation of hip rotor 575 and exoskeleton hip joint 515 is limited by the action of a hip caliper 580. Hip caliper 580 is attached to thigh link 510, with hip caliper 580 in close proximity to and selectively interacting with hip rotor 575, which is attached to hip-backpack connection 520. Person 100 controls the action of hip caliper 580 by using hand 240 to squeeze handbrake body 560 and handbrake lever 565 to transmit a force through a second brake line 585 to hip caliper 580. This force causes hip caliper 580 to engage, or contact, hip rotor 575. As hip caliper 580 engages hip rotor 575, the rotational movement of hip rotor 575 about exoskeleton hip joint 515 is impeded. Since hip rotor 575 is connected to hip-backpack connection 520, which is connecting to belt 425 of backpack 200, with belt 425 being coupled to a torso 590 of person 100, and thigh link 510 is connected to both hip caliper 580 and thigh brace 505, with thigh brace 505 being coupled to upper leg 120, the action of hip caliper 580 has the effect of limiting the movement of thigh link 510, thigh brace 505 and upper leg 120 relative to hip-backpack connection 520, belt 425 and torso 590 at hip 435. As both first brake line 570 and second brake line 585 are connected to handbrake body 560, person 100 can use hand 240 to squeeze handbrake lever 565 and handbrake body 560 to actuate both knee caliper 555 and hip caliper 580 simultaneously, thus resulting in exoskeleton device 500 resisting rotation at and limiting stress upon both knee 130 and hip 435 of person 100. Some or all of force 400 exerted by the weight of backpack 200 is transferred around person 100 through exoskeleton device 500 in this embodiment. Specifically, force 400 is transmitted from backpack 200 to belt 425 at thigh-backpack connection 525, and force 400 is then transmitted to hip-backpack connection 520 and through exoskeleton hip joint 515 to thigh link 510. Thigh link 510 transfers force 400 to thigh brace 505, which transfers force 400 over exoskeleton knee joint 530 to shank link 535. Shank link 535 transmits force 400 to boot 545, which ultimately transfers force 400 to surface 205. While the person might not control the ratio of forces between the knee and hip joints in real time, it is possible, through judicious design choice of brake and joint geometry, to keep the ratios in line with those seen in normal biomechanical data. For example, when the brakes are in the linear configuration of the second embodiment, the moment arms between the brakes and the joints are not constant. By designing the geometries of the hip and knee brake shoes, the peak moment arm at the hip and knee can be aligned with the corresponding biological peaks seen in human walking, and the braking effect across both joints would be reasonable. In the case where the brakes use a mechanical Bowden cable to transfer force, connecting both cables to the same handle assembly can be effective, although some compliance between the cables is desirable to allow for slight mechanical differences between the brake calipers.

Figure 5B:
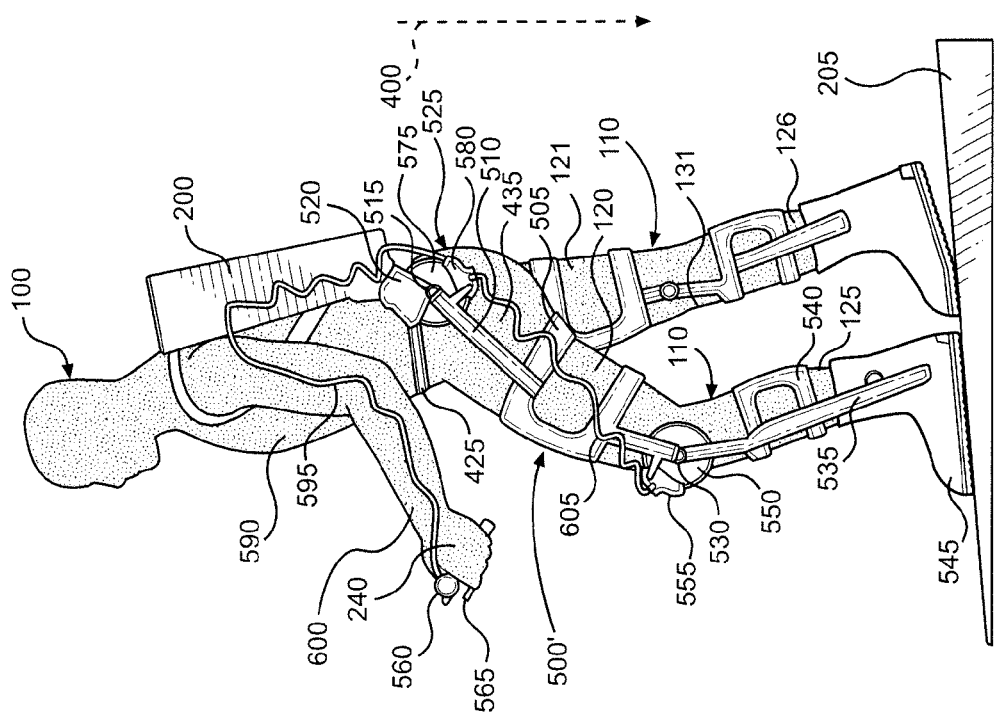
FIG. 5B is a side view of a person walking downhill while coupled to an exoskeleton device equipped with a knee braking device and a hip braking device, with the exoskeleton device coupled to the backpack, legs, and boots of the person and the brake lines attached closely to the body of the person.

Turning to FIG. 5B, a variation of the fourth embodiment is illustrated, in which an exoskeleton device 500' is configured similarly to exoskeleton device 500 from FIG. 5A. In this variation, the brake lines that control hip caliper 580 and knee caliper 555 are routed differently than first brake line 570 and second brake line 585 of exoskeleton device 500. In exoskeleton device 500', handbrake body 560 connects to an upper brake line 595, which is routed along, and possibly coupled to, an arm 600 of person 100. Upper brake line 595 is also routed along, and possibly coupled to, backpack 200. Upper brake line 595 is attached to hip caliper 580, and a lower brake line 605 extends from hip caliper 580 along upper leg 120 of person 100. Lower brake line 605 is coupled to exoskeleton device 500' at positions along thigh brace 505 and/or thigh link 510, with lower brake line 605 attaching to knee caliper 555. In this way, person 100 can use hand 240 to actuate handbrake body 560 and handbrake lever 565 to simultaneously control the action of both knee caliper 555 and hip caliper 580. In the case of a hydraulic braking system, displaced hydraulic fluid travels though the body of hip caliper 580 to lower brake line 605 and ultimately to knee caliper 555. In the case of a Bowden cable or similar system, upper brake line 595 can includes two parallel cables, with one cable terminating at hip caliper 580 and the other cable extending through lower brake line 605 to knee caliper 555. In some embodiments, upper brake line 595 is not routed along backpack 200 but rather torso 590 of person 100.

Although the embodiments of FIGS. 5A and 5B utilize rotary braking devices, the linear braking system of the second embodiment is also suitable for use in such an embodiment and may, in some cases, be preferred as it would potentiate differential braking at the hip and knee. Along these lines, it should be recognized that, for a given embodiment, the same type of braking mechanism can be used for each joint, or, alternatively, a mix of different braking mechanism can be used.

As an example of the fourth embodiment, consider a person who is on a multi-day backpacking trip over a long distance that includes a downhill descent. Due to the length of the backpacking trip, the person needs to carry more supplies, which translates into more backpack weight than this person finds comfortable (or safe) to bear during descent in the absence of the device of this embodiment. During descents, the person uses the knee and hip braking and backpack support system of the fourth embodiment to resist the motion at his knees and hips, thereby limiting the stress that would otherwise be exerted upon his knees and hips both by his own weight and the weight of the backpack. Thus, the device of this embodiment both decreases the risk of injury and possibly allows the person travel farther with the weight of his backpack, as compared with that person without the device.

In general then, the present invention is directed to an exoskeleton device comprising a first brace configured to be coupled to a first portion of a wearer and a second brace configured to be coupled to a second portion of the wearer. For purposes of the present invention, a backpack (or a part thereof) can also be considered a brace. A joint connects the first and second braces and is configured to allow relative movement between the braces. A brake, which can be selectively controlled between an unactuated state and a plurality of actuated states, is configured to impede relative movement between the first and second braces at the joint while the brake is actuated. By the brake being configured to impede movement, it is meant that the brake reduces the rate of relative movement as compared with the rate of relative movement when the brake is not actuated, i.e., when the brake is placed in the unactuated state. If desired, relative movement can be completely prevented by the brake (i.e., the brake could also assume a locked position). However, it should be understood that the actuated and unactuated states of the brake in accordance with the present invention are not intended to encompass devices, known in the prior art, where a joint is simply locked or unlocked, respectively, such that movement is either completely prevented or totally unimpeded. Instead, a manual actuator is configured to be selectively used by the wearer during relative movement between the first and second braces, and the actuator can be used to actuate the brake through a range of states in which relative movement between the braces is impeded, but not prevented, at the joint. In connection with the above, it should be recognized that the present invention provides for a range or series of actuated states with corresponding degrees of impedance, the degrees of impedance amounting to less than a locking of the brake. In other words, as with a handbrake on a bicycle, the amount of impedance provided by the brake of the present invention can be selected by a user with some granularity (for example, by varying the force exerted on the handbrake). Preferably, the exoskeleton device does not include a power source or a control system, i.e., a source of electric power or an electronic control system.

In some embodiments, the components of the exoskeleton brace and brake systems are designed so as to limit the chance of components snagging on brush or clothing (e.g., by encasing the moving parts). In some embodiments, the exoskeleton device can attach to standard backpacks while, in other embodiments, the hip joint and brake can be integral with the backpack. In some embodiments, the exoskeleton system can be modular, allowing for disconnection at various positions to provide simplified donning or doffing of the exoskeleton device or backpack. In general, as certain particular structure of an exoskeleton for use in connection with the present invention can take various forms and is known in the art, it will not be detailed further herein.

It should also be noted that the exoskeleton can simply provide a joint torque or, with more substantial torso harnessing, also provide some body weight support to the wearer of the exoskeleton device. In this latter case, the structure of the exoskeleton is preferably more substantial, but the potential is present to reduce not only the muscle load associated with hill/stair descent but also to reduce the direct bearing loads due to body weight. In some embodiments, support of the exoskeleton wearer's weight can take place in the absence of a backpack.

In some embodiments, the braking system of the exoskeleton device might not be used in preventing shock to the wearer, but, rather, a joint brake can be used to impede the movement of the joint so as to resist deliberate movements by the person wearing the exoskeleton device. For example, an athlete can wear such a device during strength or cardiovascular training. In such an embodiment, it might be preferable that the handbrake be replaced by a multiple position selection switch, not unlike the gear selector used on multi-speed bikes, that would make use of hydraulic or cable activated calipers similar to those described in above in connection with the other embodiments. The switch allows the athlete, for example, to adjust the degree to which his movement is impeded. Additionally, if desired, the switch can be placed on the structure of the exoskeleton device rather than in the hand of the wearer. Alternatively, a physical therapist or athletic trainer can use similar devices equipped with handbrakes to assist in (or impede) certain movements undertaken by patients or athletes.

In some embodiments, the exoskeleton device is equipped with a safety device proximate the joint subject to braking. The safety device is not unlike the mechanical safety mechanism commonly used in a ski boot-ski binding connection and allows for the release of the braking mechanism, the connection of the braking mechanism to an attached structural element of the exoskeleton, or the release of other component in the exoskeleton if a predetermined level of torque is experienced at the joint or in another point in the exoskeleton. The safety device would, upon activation in response to the predetermined torque threshold, serve to prevent injury to a wearer in cases when over-braking at the joint, either through user error or a brake failure of some type, would otherwise result in undesirable levels of force being experienced by the body of the exoskeleton wearer. In some embodiments, the predetermined level of torque resulting in the activation of this safety device is adjustable.

In some embodiments, the handbrake is integrated into or coupled with the structure of a walking stick, ski pole or other handheld object. In some embodiments, forces exerted by the wearer of the exoskeleton other than hand squeezing of brake controls can result in activation of the braking system. Also, rather than transmitting a force through a brake line in order to activate a braking system, a signal can be transmitted from an actuator to a brake through a wired or wireless connection.

In some embodiments, the exoskeleton device is designed to allow the braking mechanism to be distal to the joint being braked. For example, a pulley and cable system can be used to transfer the rotational force at the knee to some other point, such as the middle of the thigh, where a braking mechanism can be placed. Actuation of the braking mechanism would then result in braking of movement at the knee. Alternatively, a gear and chain system can be employed in a manner similar to that found on a bike. Such cable and pulley (or gear and chain) systems can also allow braking of both the hip and knee joints with only one braking mechanism, with this mechanism being either collocated with one joint or being located distal to both joints. This is advantageous because the brake mechanism is likely to be the most expensive part of the system. Further, differential pulley wheel size (or chain gear size) can be used as a means by which one brake mechanism can apply different levels of resisting force to knee and hip joints (or to a number of different joints). In any case, it should be recognized that there are numerous devices known in the art that allow for the transfer of force from one location to another, or the conversion of rotational force to linear force, and that can be used in connection with the present invention.

In some embodiments, brake types other than friction brakes can be used to impede the movement of exoskeleton joints. For example, an electromagnetic system can be used. While the regenerative brakes used by electric vehicles require heavy and often relatively expensive components (including electric motors and rechargeable batteries), which may be undesirable in some embodiments, simpler devices, particularly those which are lighter and cheaper, are known and are typically better suited for joint braking applications. For example, various magneto systems are commonly used to convert mechanical power from bicycles into electricity used by power bicycle lights. While similar devices can be used in connection with the present invention to provide current for lighting, power a cooling fan or any of a number of uses, one simple way to dissipate electrical energy is as heat, as seen in dynamic braking systems. As a result, an exoskeleton can be designed with an electromagnetic braking system that allows the exoskeleton wearer to actuate the brakes with differential amounts of braking by varying the amount of mechanical energy converted into electrical current, with this current later being dissipated as heat or in some other way. In some embodiments, this system is controlled by the wearer using a handbrake system similar to that used in a bicycle friction brake, with either cables or hydraulic lines interfacing with and controlling the actuation of the electromagnetic brake body itself. Such a system has advantages in terms of eliminating the need to replace frictional components, such as brake pads or shoes found in frictional brakes, while retaining the advantage of being a system that does not require the use electrical power or complex control systems to operate.

Based on the above, it should be readily apparent that the present invention provides for an unpowered exoskeleton system that does not require any electronics or batteries yet reduces the stress upon a wearer joints, particularly in connection with descending over a sloped surface with or without an added load. Although described with reference to preferred embodiments, it should be readily understood that various changes or modifications could be made to the invention without departing from the spirit thereof. In general, the invention is only intended to be limited by the scope of the following claims.

The invention claimed is:

1. An exoskeleton device comprising:
a first brace configured to be coupled to a first portion of a wearer of the exoskeleton device;
a second brace configured to be coupled to a second portion of the wearer;
a first joint connecting the first and second braces and configured to allow relative movement between the first and second braces;
a first brake controllable between an unactuated state and a plurality of actuated states, the first brake being configured to impede relative movement between the first and second braces at the first joint while the first brake is in one of the plurality of actuated states; and
a manual actuator configured to be selectively used by the wearer during relative movement between the first and second braces, wherein the manual actuator is a handbrake and use of the manual actuator causes the first brake to enter one of the plurality of actuated states such that relative movement between the first and second braces is impeded at the first joint; wherein the first brake is configured to impede, but not prevent, relative movement between the first and second braces at the first joint while the first brake is in the one of the plurality of actuated states, and the manual actuator is configured to be selectively used by the wearer during relative movement between the first and second braces.

2. The exoskeleton device of claim 1, wherein the exoskeleton device does not include a power source or a control system.

3. The exoskeleton device of claim 1, wherein the handbrake is connected to the first brake by a first brake line, and use of the handbrake actuates the first brake by transmission of force through the first brake line.

4. The exoskeleton device of claim 3, wherein:
the first brace is configured to be coupled to an upper leg of the wearer;
the second brace is configured to be coupled to a lower leg of the wearer; and
the first joint is a knee joint.

5. The exoskeleton device of claim 3, wherein:
the first brace is configured to be coupled to an upper leg of the wearer;
the second brace is configured to be coupled to a torso of the wearer; and
the first joint is a hip joint.

6. The exoskeleton device of claim 5, wherein the second brace is a backpack or a belt of a backpack.

7. The exoskeleton device of claim 3, further comprising:
a third brace configured to be coupled to a third portion of the wearer;
a second joint connecting one of the first and second braces to the third brace and configured to allow relative movement between the one of the first and second braces and the third brace; and
a second brake controllable between an unactuated state and a plurality of actuated states, the second brake being configured to impede relative movement at the second joint while the second brake is in one of the plurality of actuated states, wherein use of the handbrake causes the second brake to enter one of the plurality of actuated states such that relative movement is impeded at the second joint.

8. The exoskeleton device of claim 7, wherein the handbrake is connected to the second brake by a second brake line, and use of the handbrake actuates the second brake by transmission of force through the second brake line.

9. The exoskeleton device of claim 8, wherein the first and second brake lines are connected such that use of the handbrake actuates one of the first and second brakes by transmission of force through both the first and second brake lines.

10. The exoskeleton device of claim 8, further comprising:
the first brace is configured to be coupled to an upper leg of the wearer;
the second brace is configured to be coupled to a lower leg of the wearer;
the third brace is configured to be coupled to a torso of the wearer;
the first joint is a knee joint; and
the second joint is a hip joint.

11. The exoskeleton device of claim 1, wherein:
the first brake includes a rotor and a caliper, and use of the manual actuator causes the caliper to engage the rotor; or
the first brake includes a linear brake shoe and a caliper, and use of the manual actuator causes the caliper to engage the linear brake shoe.

12. A method of impeding relative movement in an exoskeleton device including a first brace configured to be coupled to a first portion of a wearer of the exoskeleton device, a second brace configured to be coupled to a second portion of the wearer, a first joint connecting the first and second braces and configured to allow relative movement between the first and second braces and a first brake controllable between an unactuated state and a plurality of actuated states, the first brake being configured to impede relative movement between the first and second braces at the first joint while the first brake is in one of the plurality of actuated states, the method comprising:
selectively using a manual actuator during relative movement between the first and second braces, wherein the manual actuator is a handbrake and use of the manual actuator causes the first brake to enter one of the plurality of actuated states such that relative movement between the first and second braces is impeded at the first joint; wherein the first brake is configured to impede, but not prevent, relative movement between the first and second braces at the first joint while the first brake is in the one of the plurality of actuated states, and the manual actuator is configured to be selectively used by the wearer during relative movement between the first and second braces.

13. The method of claim 12, wherein the handbrake is connected to the first brake by a first brake line, and selectively using the handbrake includes actuating the first brake by transmission of force through the first brake line.

14. The method of claim 13, wherein:
the exoskeleton device further includes:
   a third brace configured to be coupled to a third portion of the wearer;
   a second joint connecting one of the first and second braces to the third brace and configured to allow relative movement between the one of the first and second braces and the third brace; and
   a second brake controllable between an unactuated state and a plurality of actuated states, the second brake being configured to impede relative movement at the second joint while the second brake is in one of the plurality of actuated states; and
selectively using the handbrake includes causing the second brake to enter one of the plurality of actuated states such that relative movement is impeded at the second joint.

15. The method of claim 14, wherein the handbrake is connected to the second brake by a second brake line, and selectively using the handbrake includes actuating the second brake by transmission of force through the second brake line.

16. The method of claim 15, wherein the first and second brake lines are connected, and selectively using the handbrake includes actuating one of the first and second brakes by transmission of force through the first and second brake lines.

17. The method of claim 12, wherein:
the first brake includes a rotor and a caliper, and selectively using the manual actuator includes causing the caliper to engage the rotor; or
the first brake includes a linear brake shoe and a caliper, and selectively using the manual actuator includes causing the caliper to engage the linear brake shoe.

18. The method of claim 12, wherein selectively using the manual actuator includes selectively using the manual actuator while the wearer of the exoskeleton device descends over a sloped surface.

19. The method of claim 12, wherein the relative movement is initiated by the wearer initiated by the wearer.

* * * * *